(12) United States Patent
Hoendervoogt et al.

(10) Patent No.: US 8,151,801 B2
(45) Date of Patent: *Apr. 10, 2012

(54) SEPTUM PORT LOCATOR SYSTEM AND METHOD FOR AN IMPLANTABLE THERAPEUTIC SUBSTANCE DELIVERY DEVICE

(75) Inventors: Jason J. Hoendervoogt, Scottsdale, AZ (US); Scott A. Sarkinen, Greenfield, MN (US); Scott L. Kalpin, Harris, MN (US)

(73) Assignee: Medtronic, Inc., Minneapolis, MN (US)

( * ) Notice: Subject to any disclaimer, the term of this patent is extended or adjusted under 35 U.S.C. 154(b) by 4 days.

This patent is subject to a terminal disclaimer.

(21) Appl. No.: 12/872,431

(22) Filed: Aug. 31, 2010

(65) Prior Publication Data
US 2010/0331669 A1 Dec. 30, 2010

Related U.S. Application Data

(63) Continuation of application No. 11/747,614, filed on May 11, 2007, now Pat. No. 7,806,122.

(51) Int. Cl.
*A61B 19/00* (2006.01)
(52) U.S. Cl. ...................................... 128/899
(58) Field of Classification Search .................. 128/899, 128/897, 898; 600/13–14, 407, 411, 418–424; 606/1; 604/890.1, 891.1, 288.01–288.04
See application file for complete search history.

(56) References Cited

U.S. PATENT DOCUMENTS

| | | | |
|---|---|---|---|
| 3,598,903 A | 8/1971 | Johnson et al. | |
| 4,401,986 A | 8/1983 | Trenkler et al. | |
| 4,719,420 A | 1/1988 | Boimond | |
| 4,804,054 A | 2/1989 | Howson et al. | |
| 5,006,115 A | 4/1991 | McDonald | |
| 5,009,644 A | 4/1991 | McDonald | |
| 5,080,104 A | 1/1992 | Marks et al. | |
| 5,171,228 A | 12/1992 | McDonald | |
| 5,201,715 A | 4/1993 | Masters | |
| 5,375,596 A | 12/1994 | Twiss et al. | |
| 5,758,667 A | 6/1998 | Slettenmark | |
| 5,957,890 A | 9/1999 | Mann et al. | |
| 5,959,594 A | 9/1999 | Wu et al. | |
| 6,009,878 A | 1/2000 | Weijand et al. | |
| 6,287,293 B1 | 9/2001 | Jones et al. | |

(Continued)

FOREIGN PATENT DOCUMENTS
FR 2788983 A1 8/2000
(Continued)

*Primary Examiner* — Samuel Gilbert
(74) *Attorney, Agent, or Firm* — Scott A. Marks; Dicke, Billig & Czaja, PLLC

(57) ABSTRACT

An implantable medical device system includes an implantable device and an external locator device for percutaneously locating detecting port opening of the implantable device. The implantable device includes a port chamber forming the port opening, a septum sealing the port chamber relative to an exterior of the device, and a coil positioned at a known location relative to the port opening. The locator device includes a controller, at least one X-loop electrically coupled to the controller and oriented along a first major axis, and at least one Y-loop electrically coupled to the controller and oriented along a second major axis differing from the first major axis. The system is configured such that when the locator is spatially proximate the coil, an induced voltage in at least the Y-loop(s) is read by the controller to indicate a location of the coil relative to the locator device.

14 Claims, 10 Drawing Sheets

U.S. PATENT DOCUMENTS

| | | |
|---|---|---|
| 6,305,381 B1 | 10/2001 | Weijand et al. |
| 6,428,504 B1 | 8/2002 | Riaziat et al. |
| 6,689,142 B1 | 2/2004 | Tremaglio, Jr. et al. |
| 6,740,076 B2 | 5/2004 | Hoben et al. |
| 6,805,687 B2 | 10/2004 | Dextradeur et al. |
| 7,806,614 B2 * | 10/2010 | Desson et al. .............. 401/65 |
| 2004/0064030 A1 | 4/2004 | Forsell |
| 2004/0078000 A1 | 4/2004 | Borchard et al. |
| 2004/0199220 A1 | 10/2004 | Cantlon |
| 2005/0187515 A1 | 8/2005 | Varrichio et al. |
| 2008/0004642 A1 | 1/2008 | Birk et al. |
| 2008/0051722 A1 | 2/2008 | Ellsmere et al. |

FOREIGN PATENT DOCUMENTS

| | | |
|---|---|---|
| GB | 2379989 A | 3/2003 |
| JP | 07056677 | 3/1995 |
| WO | 2004/030536 A1 | 4/2004 |

* cited by examiner

SEPTUM PORT LOCATOR SYSTEM AND METHOD FOR AN IMPLANTABLE THERAPEUTIC SUBSTANCE DELIVERY DEVICE

CROSS-REFERENCE TO RELATED APPLICATIONS

This application is a continuation of U.S. Ser. No. 11/747,614, filed May 11, 2007 and entitled "Septum Port Locator System and Method for an Implantable Therapeutic Substance Delivery Device"; the entire teachings of which are incorporated herein by reference.

BACKGROUND

The present disclosure relates to implantable medical devices for delivering a liquid therapeutic substance to a delivery site within a patient. More particularly, it relates to systems and methods for percutaneously locating one or more septum ports of the implantable medical device.

A variety of implantable medical devices are available for treating patients. For example, implantable substance delivery devices are typically used to deliver infusion media or therapeutic substances (such as medication) to a patient at a regulated dosage. The implantable substance delivery device (sometimes referred to as a drug pump) is implanted by a physician into a patient at a site appropriate for the therapy. Typically, an infusion catheter is connected to an outlet of the device, and is implanted/positioned to infuse the therapeutic substance at the desired therapy site so as to treat a condition such as pain, spasticity, cancer, neurodegenerative diseases, trauma, diabetes, or other medical conditions. The term "implantable substance delivery device" as used herein refers to any implantable device for delivering medicaments including, but not limited to, bladder pumps, accumulator pumps, fixed-rate bellows pumps, and the like, as well as implantable devices that do not necessarily include a pump.

In general terms, the implantable substance delivery device commonly includes a drug reservoir containing a volume of the infusion media, and a pump and/or metering mechanism to propel the infusion media in some metered or other desired flow dosage to the therapy site from the reservoir via the catheter. Over time, the therapeutic substance in the reservoir becomes depleted and it is necessary to refill the device with a new supply of therapeutic substance. In order to avoid surgically accessing and refilling the device, it is desirable to have the ability to percutaneously refill the drug reservoir. This is commonly done by providing the delivery device with a fill port assembly that includes a fill port establishing fluid access to the drug reservoir from an exterior of the device. In this regard, a resilient, resealable septum is provided with the fill port assembly, and is accessible by percutaneously inserting a hypodermic needle through the skin and then the septum via a fill port opening provided at the device's exterior. Once the septum has been pierced, the hypodermic needle is fluidly connected to the drug reservoir such that the reservoir can be refilled. Additional septum-type port assemblies can also be provided with the implantable device, such as a catheter access port assembly.

Because the device is implanted within the patient and cannot be seen directly, care must be taken to ensure that the needle is properly placed into the fill port assembly before transferring liquids. If the needle is not located within the fill port assembly (e.g., does not pass through the fill port opening; is mistakenly inserted into the catheter access port; the needle does not pierce the septum; etc.), delivery of the infusion media through the needle can result in immediate delivery of a significant quantity of the drug to the patient, with potentially adverse consequences. In addition, unintended failure to properly refill the drug reservoir may lead to complications for the patient when the needed medication is not dispensed at a later time. Other concerns may arise for a clinician intending to deliver liquids to and through the catheter access port; if the fill port is instead mistakenly accessed by the needle, an undesired liquid may be filled into the drug reservoir leading to potential complications.

In light of the above, efforts have been made to identify to the clinician a location of the fill port assembly (and/or the catheter access port assembly) relative to the patient's skin prior to insertion of the needle. For example, templates are well known, and can provide a general indication or map of the fill port and/or catheter access port location(s) following palpating the device's periphery through the patient's skin. Additionally, electronic and/or magnetic systems have been suggested that may provide the clinician with additional information generally indicative of the port assembly position. Due to the importance of accurately locating the desired port opening, any improvements in this area would be well-received. As implantable therapeutic substance devices become increasingly reduced in size, correctly locating the desired port assembly or opening has become increasingly more difficult as the ports are located in relatively close proximity to one another.

In light of the above, a need exists for improvements in percutaneously locating a port assembly of an implantable medical device.

SUMMARY

Aspects in accordance with principals of the present disclosure relate to an implantable medical device system. The system includes an implantable substance delivery device and an external locator device for percutaneously locating a fill port (or opening thereto) of the implantable medical device. The implantable medical device includes a housing maintaining a reservoir for containing a therapeutic substance, and a fill port assembly defining a port chamber having a fill port opening and in fluid communication with the reservoir. The implantable medical device also includes a coil located at a known position relative to the fill port opening. The external locator device includes a controller and a locator grid. The locator grid has at least one X-loop electrically coupled to the controller and oriented along a first major axis, and at least one Y-loop electrically coupled to the controller and oriented along a second major axis differing from (e.g., orthogonal to) the first major axis. In this regard, the system is configured such that when the locator is spatially proximate the coil and the coil is energized, the energized coil induces a voltage in the Y-loop(s) that is read by the controller. The controller, in turn, is adapted (e.g., programmed) to determine a location of the coil relative to the locator grid based upon the read signal, as well as to optionally locate the fill port opening based upon the determined location of the coil. In some embodiments, the system is configured such that the coil is energized by the external locator device (e.g., by a current supplied to one or more of the X-loops); in other embodiments, the coil is energized by a power source carried by the implantable medical device. The coil can be optionally co-axially centered about the fill port opening in some embodiments, and can be spaced or off-set from the fill port opening in other optional embodiments.

Yet other aspects in accordance with principals of the present disclosure relate to a method of locating a port opening of a medical substance delivery device implanted at an implant site in a patient from a location external the patient's skin. The method includes providing a coil coupled to the medical device and positioned at a pre-determined location relative to the port, and placing an external locator proximate the coil. In this regard, the device includes a controller electrically coupled to at least one X-loop oriented along a first major axis and at least one Y-loop oriented along a second major axis that differs from (e.g., is orthogonal) to the first major axis. The method additionally includes energizing the coil and sensing a signal that is induced in at least one of the Y-loops by the energized coil. A location of the coil is determined, based at least in part, upon the sensed signal. The method ultimately includes locating the port opening based upon the determined location of the coil. In some embodiments, a plurality of Y-loops are provided, and the location of the coil is determined by comparing induced voltage signals generated at each of the Y-loops with one another to identify a peak value, optionally on an iterative basis.

DETAILED DESCRIPTION

Figure 1:
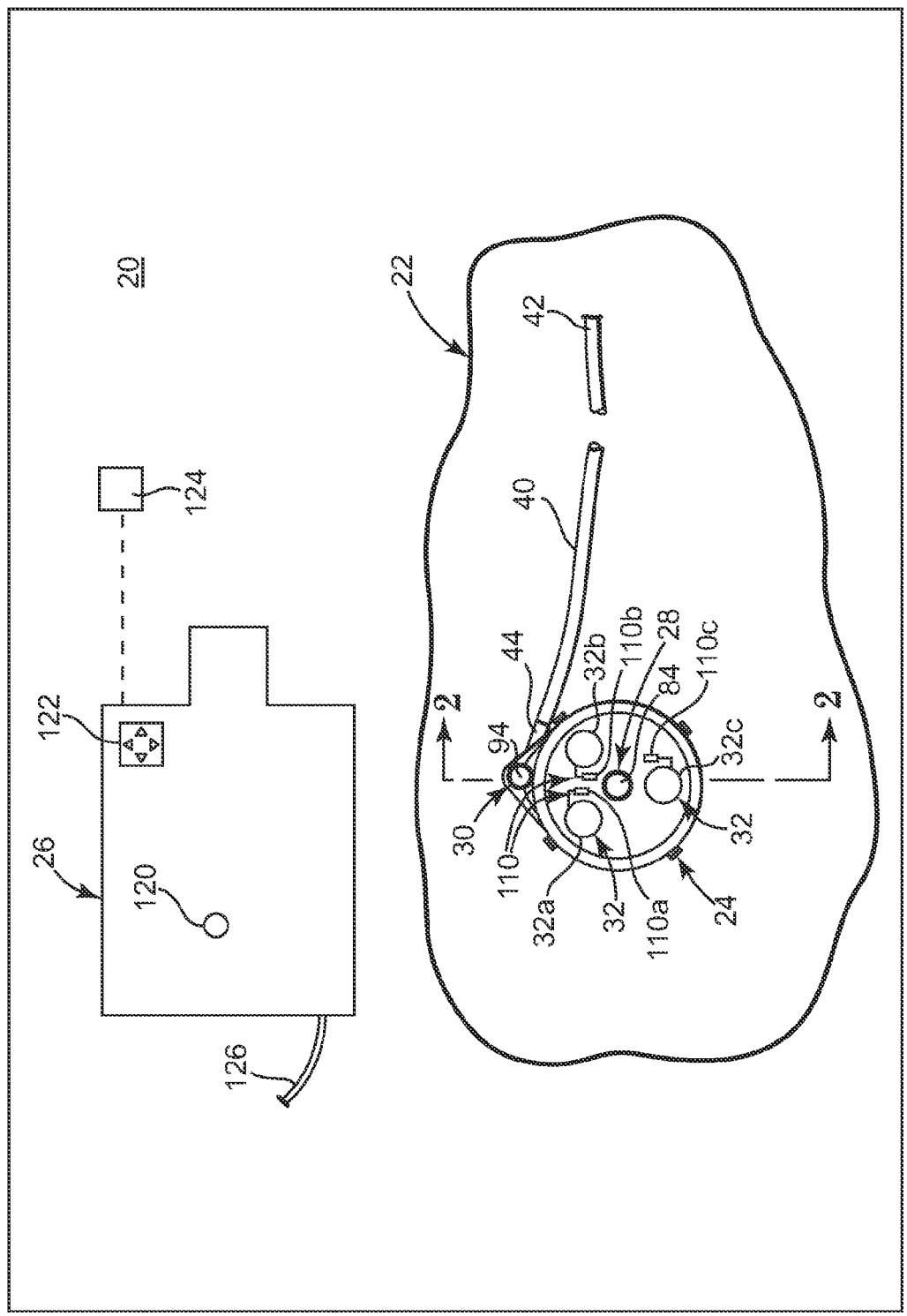
FIG. 1 is a schematic top view of an implantable medical substance delivery device system in accordance with principles of the present disclosure.

FIG. 1 illustrates a schematic top view of one embodiment of an implantable medical device system 20 in accordance with principles of the present disclosure, as applied to a patient 22 site (drawn generally) as one example of a suitable environment for effectuating a treatment. The system 20 includes an implantable substance delivery device 24, also known as a drug pump, and an external locator device 26. In other embodiments, the system 20 can further include a remote programmer (not shown) for interfacing with the delivery device 24 from a point outside of the patient 22. Details on the various components are provided below. In general terms, however, the implantable device 24 includes various components normally associated with implantable therapeutic substance delivery devices, including a fill port assembly 28 and a catheter access port assembly 30. In addition, the implantable device 24 includes one or more coils 32 (referenced generally) that electrically interface (e.g., induced voltage) with circuitry loops provided with the locator device 26 in prompting the locating device 26 to determine and indicate a location of the fill port assembly 28, the catheter access port assembly 30, or both, at a location external the patient 22 (i.e., percutaneously).

With the above in mind, the substance delivery device 24 can assume a number of forms suited to provide a variety of therapies to treat medical conditions (also known as medical indications) such as pain, spasticity, cancer, and as well as other medical conditions. The delivery device 24 is typically implanted at the patient 22 site in a suitable surgical procedure performed under a suitable anesthesia. Before or concurrent with implanting the delivery device 24, a catheter 40 is typically implanted such that a distal end 42 is positioned at a desired infusion site, and a proximal end 44 is tunneled to a location where the delivery device 24 is to be implanted. In alternative embodiments, the delivery device 24 is configured to deliver therapeutic substances directly to the patient 22 such that the catheter 40 can be eliminated.

The delivery device 24 is generally implanted subcutaneously (i.e., beneath the skin) relative to the patient 22 at a site having sufficient subcutaneous tissue to support the device 24. Once implanted, the delivery device 24 operates to infuse a therapeutic substance (not shown) at a desired or calculated rate into the patient. As is known in the art, the therapeutic substance is a compound intended to have a therapeutic effect, and can include pharmaceutical compositions, genetic materials, biologics, and other suitable substances. Other suitable substances that are not easily classified, but are likewise intended to have a therapeutic effect, can be infused and include saline solution, fluoroscopy agents, and the like.

Figure 2:
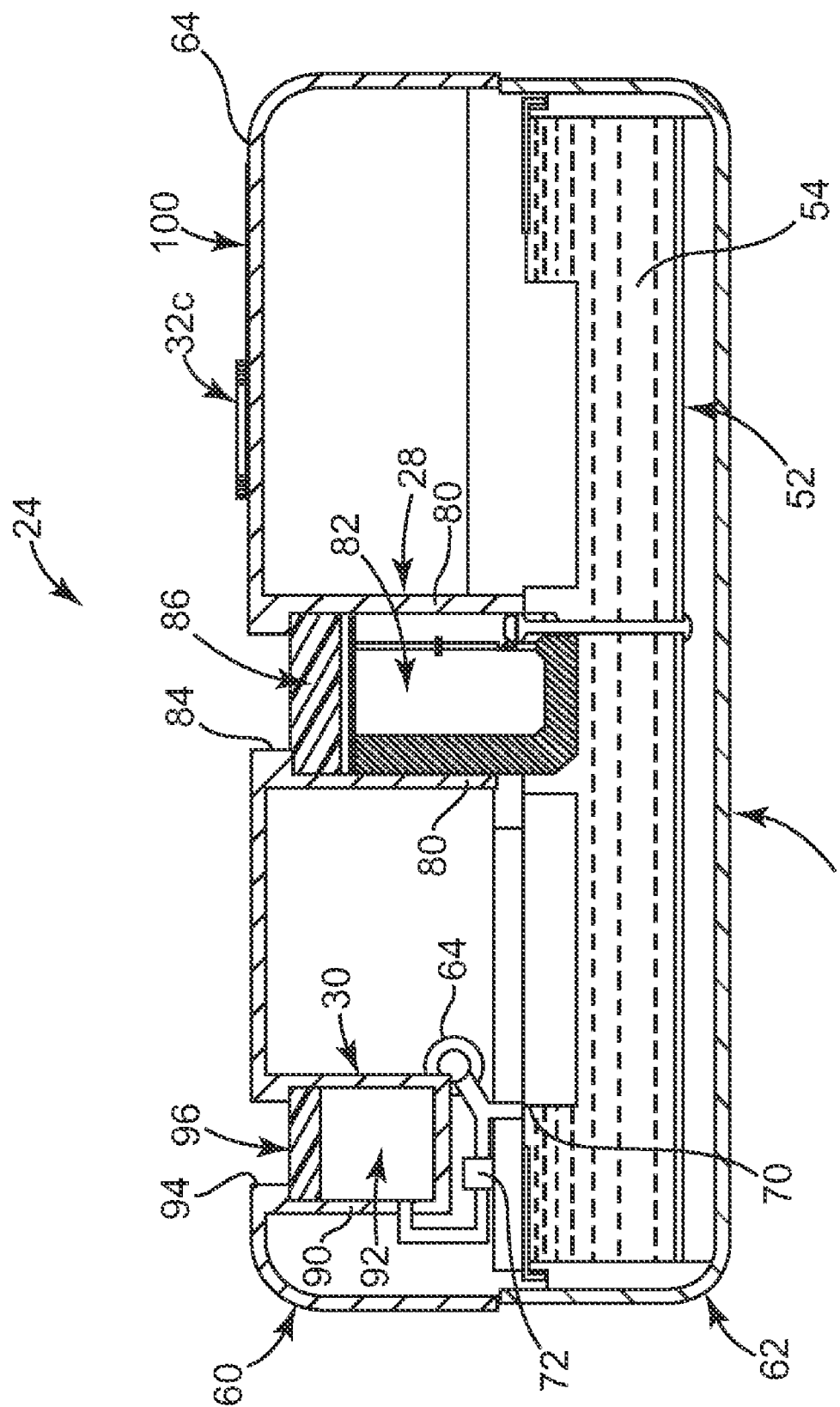
FIG. 2 is a cross-sectional view of an implantable substance delivery device of the system of FIG. 1.

For a range of reasons, not the least of which are patient comfort and convenience, the implantable delivery device 24 defines access ports, such as the fill port assembly 28 and the catheter access port assembly 30, that are configured to be percutaneously accessed by a hypodermic syringe (not shown). The port assemblies 28, 30 can generally assume any format conventionally employed, and are shown in greater detail in FIG. 2. The implantable delivery device 24 further includes a housing 50 that maintains or forms a reservoir 52, the fill port assembly 28, and the catheter access port assembly 30. The housing 50 further maintains other components of the delivery device 24 (such as a power supply (not shown) and related circuitry), and the reservoir 52 contains (filled or partially filled) a desired liquid-therapeutic substance 54.

In some embodiments, the housing 50 is formed of an inert (i.e., non-reactive) and rigid material selected to be suited for surgical implantation into a human body. Suitable inert and rigid materials include metals including precious metals and/or titanium, and biologically inert polymers, for example. Regardless, the housing 50 can be formed to include or define a first section 60 and a second section 62 that combine to define an exterior 64 of the implantable delivery device 24. When assembled, the first and second sections 60, 62 contain the reservoir 52. In addition, the housing 50 includes a discharge outlet 64 that is configured to be fluidly coupled to the proximal end 44 of the catheter 40 (FIG. 1). A reservoir outlet 70 fluidly connects the reservoir 52 and the discharge outlet 64, providing a pathway for the therapeutic substance 54 to flow from the reservoir 52 to the discharge outlet 64, and ultimately through the catheter 40 to the patient site. To this end, the reservoir 52 can include or form a variety of structures or mechanisms useful to facilitate continuous, positive availability of the therapeutic substance 54 at the reservoir outlet 70, such as bellows that are acted upon by a propellant, as is known in the art. Further, in some embodiments, a metering mechanism 72 as is known in the art can be provided to assist in directing or controlling flow of the therapeutic substance 54 from the reservoir outlet 70.

With the above background in mind, the fill port assembly 28 provides a fluid connection to the reservoir 52 from an exterior of the implantable delivery device 24, and includes a port wall 80 that defines a port chamber 82 configured to communicate with the exterior 64 of the delivery device 24 through or at a fill port opening 84. The fill port assembly 28 further includes a septum 86 that is provided to seal the port chamber 82 relative to the fill port opening 84 (and thus relative to the device exterior 64). The fill port assembly 28 thus provides a sealed structure through which the reservoir 52 can be percutaneously accessed via the fill port opening 84 (e.g., for filling the reservoir 52).

The catheter access port assembly 30 similarly includes a wall 90 that defines a well 92 that communicates with the exterior 64 of the delivery device 24 through a catheter access port opening 94. A septum 96 is further provided that seals the well 92 relative to the device exterior 64. Further, a fluid pathway 98 is defined between the well 92 and the discharge outlet 64. The catheter access port assembly 30 thus provides a sealed structure through which fluid can be directly flowed to the discharge outlet 64 (and thus the catheter 40 (FIG. 1)), effectively bypassing the reservoir 52.

Regardless of a specific structure of the port assemblies 28, 30, the septums 86, 96 are generally formed of resilient, resealable material, such as silicone rubber, that is durable enough to withstand numerous percutaneous hypodermic needle punctures without leaking. In this manner, the reservoir 52 can be percutaneously filled by inserting a needle (not illustrated but known in the art) through the patient's skin, through the fill port opening 84, and through the respective septum 86. Once the hypodermic needle punctures the septum 86, the therapeutic substance 58 can be injected through the hypodermic needle and into the reservoir 52. Similarly, percutaneous direct delivery of liquid to the patient 22 can be accomplished via a needle passed through the septum 96 of the catheter access port assembly 30.

The above features of the implantable delivery device 24 are known. Commensurate with these, and other features, then, the delivery device 24 can, in general terms, be of any suitable, implantable design for temporarily storing and subsequently dispensing a liquid therapeutic substance at a metered rate, such as a SynchroMed® EL implantable drug pump or an IsoMed™ constant flow infusion system, both available from Medtronic, Inc. of Minneapolis, Minn.; a Paradigm® insulin pump available from Medtronic-MiniMed, Inc. of Northridge, Calif.; etc. Further, any other implantable therapeutic substance delivery devices currently known or in the future contemplated can also be used in connection with principles of the present disclosure.

Regardless of an exact construction and features provided, the implantable delivery device 24 further includes the coil(s) 32. With combined reference to FIGS. 1 and 2, one or more of the coils 32 can be provided. Thus, for example, while FIG. 1 reflects three of the coils 32a, 32b, 32c, in other embodiments only one or two of the coils 32 can be included; yet other embodiments include four or more of the coils 32. In general terms, each of the provided coils 32 are formed or provided at a known or pre-determined location relative to the fill port opening 84 and the catheter access port opening 94 (e.g., relative to the X, Y plane of FIG. 1). As made clear below, when energized, each of the coils 32 provide a distinct signal recognized by the external locator 26, with the external locator 26 adapted to interpret these signal(s) to determine a location of the coil(s) 32. Based upon the known location of the coil(s) 32 relative to the fill port opening 84 and the catheter access port opening 94, the locator 26 operates to locate the desired port opening 84 or 94; visually indicate a direction the locator 26 should be moved to be in closer proximity to the desired port opening 84 or 94; as well as visually indicate a location of the desired port opening 84 or 94 when a corresponding segment of the locator 26 is positioned substantially directly over the desired port opening 84 or 94. Thus, for example, where the three coils 32a-32c are provided, each of the coils 32a-32c are off-set from the port openings 84, 94, defining a triangle; when a center of each of the triangularly-arranged coils 32a-32c is percutaneously determined, a location of the desired port opening 84 or 94 is then effectively "known."

Figure 3A:
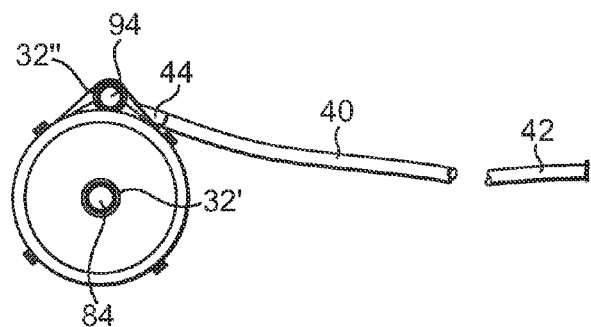
FIG. 3A is a simplified top view of another implantable substance delivery device useful with the system of FIG. 1.
Figure 3B:
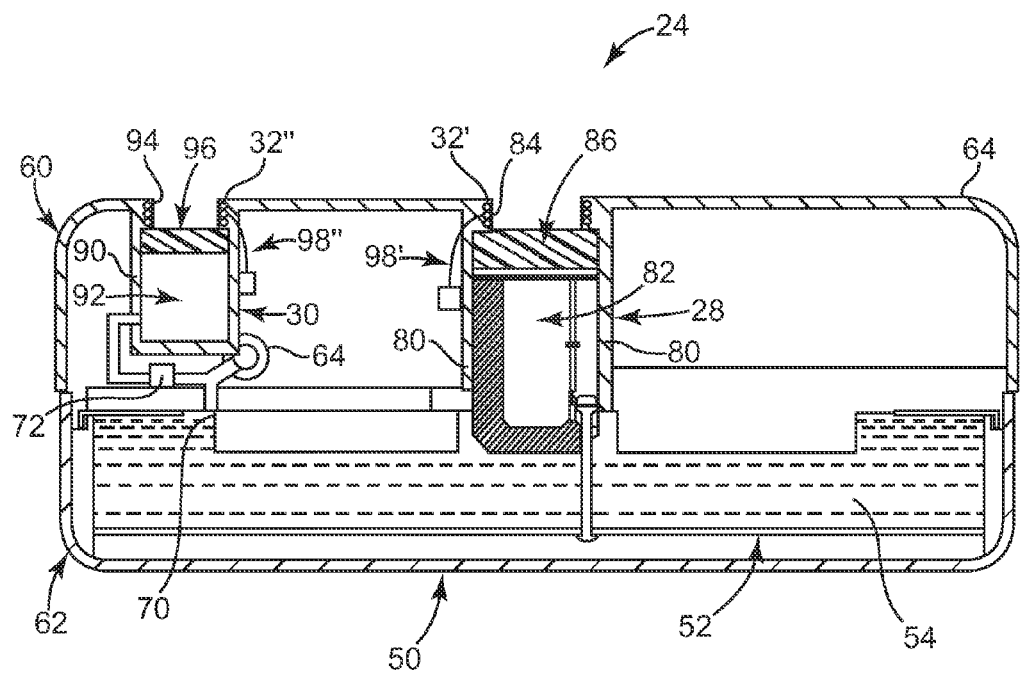
FIG. 3B is a cross-sectional view of the delivery device of FIG. 3A.

Alternatively, and as shown FIGS. 3A and 3B, a first coil 32' can be co-axially centered about the fill port opening 84, and a second coil 32" can be co-axially centered about the catheter access port opening 94. With this approach, when determining a location of the first coil 32', the location of the fill port opening 84 is also effectively known or determined; a similar relationship is established for the second coil 32"/ catheter access port opening 94. As a point of reference, FIG. 3B reflects additionally exemplary circuitry 98', 98" that can be used in connecting the coils 32', 32" to a power supply (not shown), of the delivery device 24 with active construction embodiments as described below. A number of other coil configurations are also envisioned. For example, only a single one of the coils 32 (FIG. 1) need be provided, for example, co-axially centered about the fill port opening 84 (under these circumstances, the system 20 would operate to only indicate a location of the fill port assembly 28 that is otherwise of primary concern). Once again, in yet other embodiments, four or more of the coils 32 can be included, and all or some of the provided coils 32 can be off-set from, or co-axially aligned with, the port openings 84, 94. Regardless, the coil(s) 32 are formed of or include metal and thus can be energized in the presence of an electrical-type field (e.g., an applied current, an electromagnetic field, etc.).

Returning to FIGS. 1 and 2, in some embodiments, the coil(s) 32 are "passive" in that are not directly powered by a power source (not shown) or internal circuitry of, or carried by, the implantable delivery device 24. Instead, as explained below, the external locator device 26 includes one or more loops that when energized in proximity to the coil(s) 32, serves to energize the coil(s) 32 as a function of the distance between the energized loop and the coil 32 being located. Alternatively, the coil(s) 32 can be directly electrically coupled to the power source and internal circuitry of implantable medical device 24, thus creating an "active" configuration (i.e., the locator device 26 does not operate to energize the coil 32 being located). Operations of the "passive" and the "active" constructions are described in greater detail below.

The coil(s) 32 can be assembled or provided relative to the housing 50 in a variety of fashions. For example, the coil(s) 32 can be formed on, or as part of, a flex circuit 100 that is otherwise assembled to the housing 50. The flex circuit 100 can further establish an electrical connection to the device's 24 power source (not shown) with the active construction. Alternatively, and as shown in FIG. 3B, the coil(s) 32 (e.g., the coils 32', 32") can be embedded into the housing 50 (e.g., with the port wall 80 or 90, respectively).

Regardless of an exact construction, in some embodiments, a tuning capacitor 110 is provided for each of the coils 32, as represented schematically in FIG. 1. Thus, where the implantable delivery device 24 includes the three coils 32a-32c, three of the tuning capacitors 110a-110c are also provided, each electrically connected in parallel with a corresponding one of the coils 32a-32c. Each combination coil 32/tuning capacitor 110 forms a tank circuit (e.g., the first coil 32a and the first tuning capacitor 110a form a first tank circuit). For passive constructions, the tank circuits (where two or more of the coils 32 are included) are "tuned" to different, known frequencies (e.g., the first tuning capacitor 110a "tunes" the first coil 32a to a first frequency). During use, the external locator 26 selectively generates an electrical field at the different frequencies to individually "locate" the coils 32 as described below. In other words, the tuning capacitors 110 serve to differentiate signals generated by the coils 32 from one another (e.g., the external locator 26 can operate to energize at the first frequency in locating the first coil 32a; at the second frequency in locating the second coil 32b; etc.).

For active constructions, the coils 32 can be directly energized by the delivery device's 24 power source at different frequencies via active circuitry carried by the delivery device 24 (e.g., oscillators). The tuning capacitors 110 can still be included, serving primarily to improve an efficiency of converting current flow through the corresponding coil 32 into an electromagnetic field to be sensed by the locator device 26 (thereby addressing possible signal attenuation in the presence of the metallic housing 50 (FIG. 2)). As a point of reference, coil differentiation with the active construction can be achieved in other manners, such as by "driving" the coils 32 sequentially for different, pre-determined lengths of time, in a pattern "recognized" by the locator 26 (e.g., first coil 32a is energized for a first time period T and the second coil 32b is energized for a second time period 2T, etc.). Yet another technique or means for distinguishing one coil from another (e.g., distinguishing the first coil 32a from the second coil 32b) is to periodically modulate the carrier with a modulation scheme of a type known in the art such as AM, FM, FSK, etc., to communication and uniquely identify which coil is being energized.

With the above construction of the implantable delivery device 24 in mind, the external locator device 26 operates to locate one or both of the fill port opening 84 and the catheter port opening 94 from a location exterior to the patient 22 site. In particular, the external locator device 26 is configured to selectively detect and determine, through electromagnetic interactions, a location of the coil(s) 32 and, based upon the determined locations, locate the desired port opening 84 or 94. In this regard, in the passive embodiment described above, the coils 32 interact with or otherwise respond (i.e., become energized) to an electromagnetic field of the external locator device 26. In some embodiments, the external locator device 26 further defines a needle opening 120 that extends through the external locator device 26, and a visual indicator 122 that provides real-time feedback/data output that guides a clinician in aligning the needle opening 120 with a selected one of the port openings 84, 94.

The visual indicator 122 can be configured to identify a position of the locator device 26, and in particular the needle opening 120, relative to a desired, targeted port openings 84, 94 based upon sensing one or more of the coils 32 as described below. The visual indicator 122 can be a lighted indicator, such as a light emitting diode, or other suitable light source. In other embodiments, the external locator device 26 communicates its real-time position data wirelessly to a remote visual indicator 124 that enables the clinician to guide the needle opening 120 over a selected one of the port openings 84, 94. Regardless, the external locator device 26 is configured or programmed to enable the clinician to quickly and accurately identify, from a point exterior to the patient 22 site, where one of the port openings 84, 94 is located. In this manner, the clinician is able to properly place a needle of a syringe (not shown, but known in the art) into a desired one of the port openings 84, 94 prior to transferring liquids into the delivery device 24. To this end, although not shown to scale, the needle opening 120 is sized to provide an opening on the order of about 0.005-0.10 inches to accommodate a needle of the syringe, although other dimensions are also acceptable.

In one embodiment, the external locator device 26 is a powered locator device that includes a hard-wired power cord 126 configured to be electrically connected to a source, such as a power outlet in a wall, for example. In alternative embodiments, the external locator device 26 is battery powered.

Figure 4:
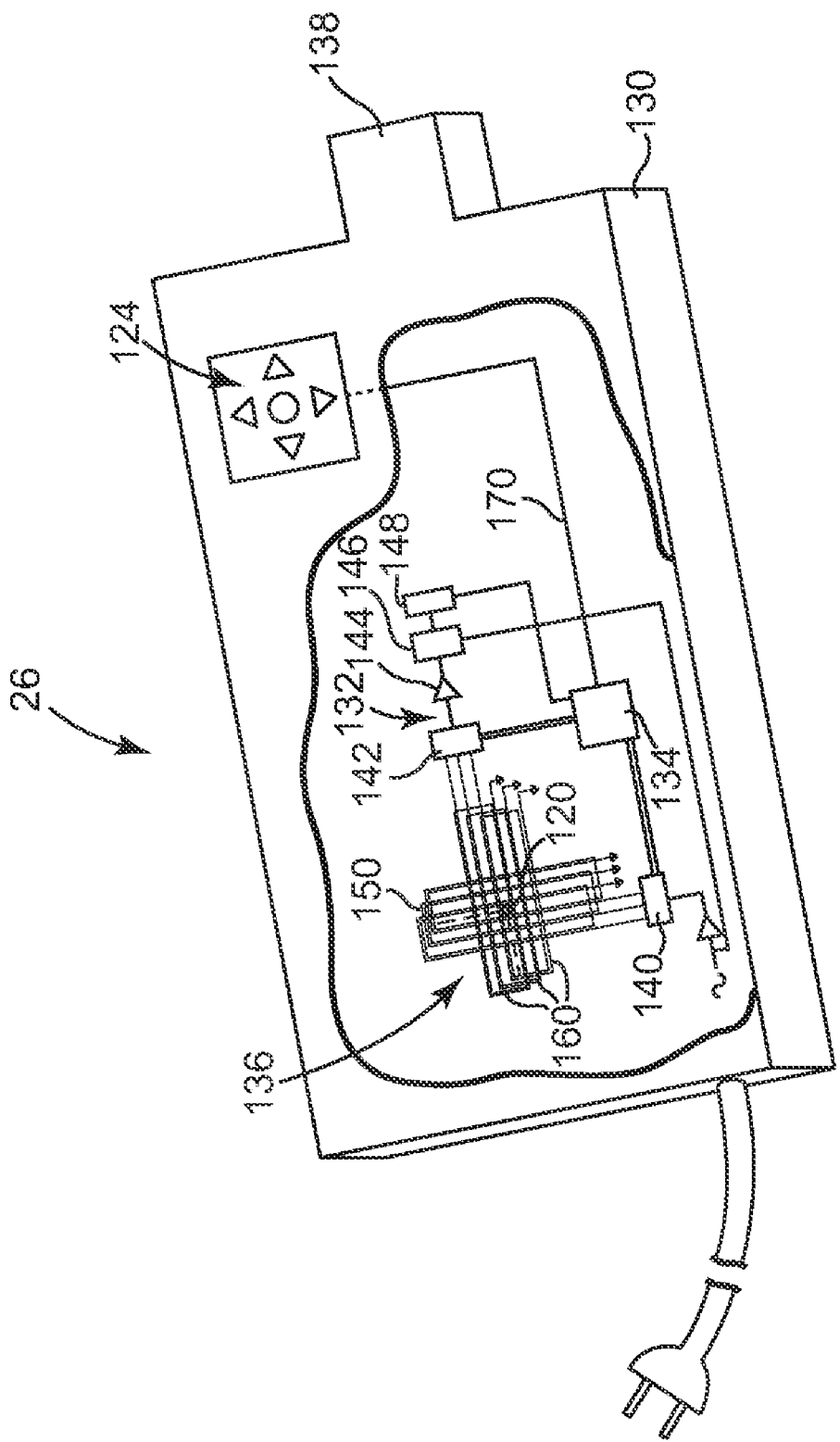
FIG. 4 is a perspective illustration of an external locator device of the system of FIG. 1 having a portion cutaway to illustrate circuitry in accordance with principles of the present disclosure.

FIG. 4 illustrates a perspective view of the locator device 26 having a cutaway portion that schematically illustrates circuitry of the device 26 in accordance with some embodiments. The locator device 26 generally includes a case 130 maintaining or enclosing circuitry 132 (referenced generally) including a controller 134 that is electrically coupled to a locator grid 136.

In some embodiments, the case 130 optionally includes or forms a tab 138 that defines a handle suitably sized to be grasped by a clinician or other user of the external locator device 26. For example, the external locator device 26 can have has a mass of between about 1-12 ounces, and the tab 138 is sized to enable the clinician to grasp the tab 138 between a thumb and finger in manipulating/moving the device 26 relative to the patient 22 site (FIG. 1). A wide variety of other constructions are also acceptable that may or may not include the handle/tab 138. The case 130 can be formed of a plastic material such as polyethylene, polyester, and nylon, although other suitable plastics such as thermosets are also acceptable.

The circuitry 132 is generally printed, wired or otherwise suitably disposed onto a board, such as a printed circuit board or wiring board. In some embodiments, the circuitry 132 includes a drive multiplexer 140 in electrical communication with the locator grid 136, a receiver multiplexer 142 that likewise is in electrical communication with the locator grid 142, an amplifier 144, a synchronous demodulator 146, and an analog to digital signal converter 148, each of which is electrically coupled to the controller 134. In this regard, the controller 134 can be a micro-controller that is configured or programmed to time, sense, stage, etc. electrical signals input to and output from the locator grid 136.

The locator grid 136 includes at least one X-loop 150 electrically coupled to the controller 134, and at least one Y-loop 160 electrically coupled to the controller 134 and generally oriented in a direction differing from (e.g., orthogonal to) the X-loop 150, as more fully described below. In general, the needle opening 120 extends through the case 130 and is located centrally relative to the locator grid 136. Any other number of the X-loops 150 and the Y-loops 160 can be included. Thus, and with reference to FIG. 5, the locator grid 136 can include three of the X-loops 150a-150c and three of the Y-loops 160a-160c, although other numbers, either greater or lesser, are acceptable.

As mentioned above, the system 20 (FIG. 1) can have either a passive construction (i.e., the coil(s) 32 (FIG. 1) are passively energized by the locator device 26) or an active construction (i.e., the coil(s) 32 are directly energized by the delivery device's 24 (FIG. 1) power source). For passive applications, the locator device 26 is powered, for example by the power cord 126, to drive a current through the drive multiplexer 140 and through and around the X-loop(s) 150 (or a selected one of the X-loops 150) in a manner dictated by the controller 134. The current flowing through the X-loop 150 creates a magnetic field. Under these and other passive-type applications, it is desirable that the differing orientation of the X-loop(s) 150 relative to the Y-loop(s) 160 (i.e., orientation of a major axis of the X-loop(s) 150 relative to the orientation of a major axis of the Y-loop(s) 160) provide a substantially orthogonal relationship to minimize direct electrical interface between the X-loop(s) 150 and the Y-loop(s) 160. That is to say, in some embodiments, the X-loop(s) 150 are generally oriented orthogonally to the Y-loop(s) 160, such that the X-loop(s) 150 and the Y-loop(s) 160, as an example, are electrically decoupled and the magnetic field generated by the current flowing through the X-loop(s) 150 will not induce any voltage in any selected ones of the Y-loop(s) 160. However, in the presence of a coil, such as the coil(s) 32 (FIG. 1), the magnetic field generated by current flowing through the X-loop 150 will induce a voltage in the coil, thereby causing a current to flow in the coil. For passive constructions, then, the so-generated current generates a magnetic field, thereby inducing a voltage in the Y-loop(s) 160 that is received by the receiver multiplexer 142. With the above in mind, for passive constructions the X-loop(s) 150 can be designated as drive loop(s) that drive current in the locator grid 136, and the Y-loop(s) 160 can be designated as receive loops. For active constructions, the X-loop(s) 150 and the Y-loop(s) 160 all effectively serve as receive loops, and need not have an orthogonal relationship.

The signal received by the receiver multiplexer 142 is amplified by the amplifier 144, demodulated (i.e., rectified to provide DC magnitude and phase information) by the demodulator 146, and converted by the analog to digital converter 148 into a digital number that can be processed by an algorithm programmed into the controller 134. In some embodiments, the demodulator 146 is adapted to rectify an alternating current (AC) signal from the receiver multiplexer 142 and capture signal information, such as a magnitude of the signal amplitude and, for passive constructions, the signal phase (either in-phase with the drive signal or 180 degrees out-of-phase with the drive signal), exiting the receiver multiplexer 142. The phase information is used to determine whether the coil 32 (FIG. 1) being located is within a selected drive/X-loop 150 or receive/Y-loop 160 (in-phase), or outside of the selected loop (180 degrees out-of-phase) as described below. The analog to digital converter 148 converts the alternating signal in its analog form into a digital output readable by the controller 134. In this regard, the controller 134 can be a microprocessor including an electronic chip, such as a silicon chip, that is configured to logically control digital data input and output to the circuitry 132. For passive constructions, the controller 134 can be programmed to energize the drive loop(s) 150 at distinct frequencies, corresponding with those associated with the tank circuits/coils 32 (FIG. 1) described above. For example, with the one embodiment in which three of the coils 32a-32c and the tuning capacitors 110a-110c are provided, and thus three distinct coil frequencies, the controller 134 is adapted or programmed to promote energization of the drive loops 150 at each of the three, known frequencies.

Other suitable circuitry that is sensitive to or configured to detect the presence of a metal coil within at least one of the X-loop(s) 150 and the Y-loop(s) 160 is also acceptable. That is to say, in some embodiments one or more of the components of the circuitry 132 can be replaced with a single functionally equivalent component, for example.

As mentioned above, the locator grid 136 can include a plurality of the X-loops 150 and a plurality of the Y-loops 160 that are individually sensitive to the presence of a coil, and the controller 134 includes an output line 170 that electrically communicates with the visual indicator 122. In this manner, a relative location of the locator grid 136 to a selected coil is sensed by the circuitry 132 and communicated as an output signal to the indicator 122. Thus, a clinician using the external locator device 26 can be guided by the visual indicator 122 and prompted to move the locator device 26 to locate one or both of the port openings 84, 94 (FIG. 1).

Figure 5:
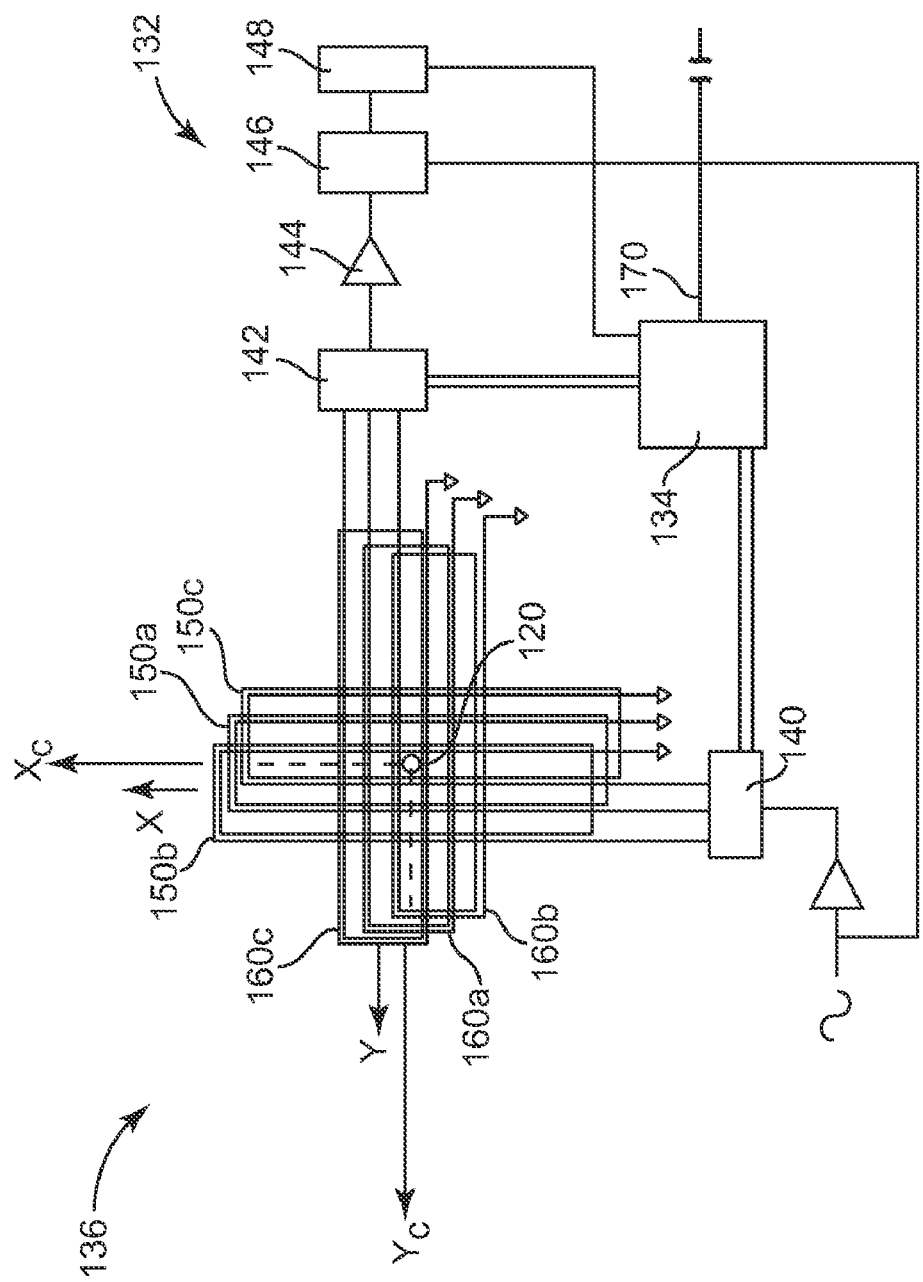
FIG. 5 is a schematic illustration of the circuitry of FIG. 4.

With the above in mind, the locator grid 136 is represented in FIG. 5 with an X-Y major axis superimposed. With the one embodiment shown, the locator grid 136 includes a central X-loop 150a, and the second and third X-loops 150b, 150c that are parallel to the central X-loop 150c. For example, the X-loops 150a-150c are oriented parallel relative to the major X axis, and the X-loops 150a-150c are spaced relative to each other such that the second X-loop 150b is parallel to but offset from the central X-loop 150a, and the third X-loop 150c is parallel to and offset from the central X-loop 150a and the second X-loop 150b. In this regard, the central X-loop 150a defines a central axis $X_C$ that is parallel to the X axis and central to the X-loops 150a-150c.

Similarly, the plurality of Y-loops 160 includes a central Y-loop 160a, the second Y-loop 160b, and the third Y-loop 160c. Generally, the Y-loops 160 are oriented parallel relative to the major Y axis, and orthogonal to the X-loops 150. For example, in one embodiment the central Y-loop 160a is oriented along a central axis $Y_C$, the Y-loops 160a-160c are oriented parallel relative to the Y axis, and the Y-loops 160a-160c are spaced relative to each other such that the second Y-loop 160b is parallel to but offset from the central Y-loop 160a, and the third Y-loop 160c is parallel to and offset from the central Y-loop 160a and the Y-loop 160b.

With the above description in mind, it is to be understood that the locator grid 136 can, and preferably does, include more than the three illustrated X-loops 150a-150c and more than the three illustrated Y-loops 160a-160c. In this regard, although it is within the scope of the present disclosure to provide the locator grid 136 with a single one of the X-loops 150 and a single one of the Y-loops 160, in a preferred embodiment the locator grid 146 includes many multiple X-loops 150 oriented as illustrated above, and many multiple Y-loops 160 oriented orthogonal to the X-loops 150.

In one embodiment, the locator device 26 (FIG. 4) defines the needle opening 120 at a location where the central axis $X_C$ intersects with the central axis $Y_C$. In this manner, the needle opening 120 is disposed centrally to the locator grid 136, in the middle of the central X-loop 150a and in the middle of the central Y-loop 160a.

The X-loops 150 can include electrical wires or printed circuitry that is configured such that the X-loops 150 generally overlap one or more of each other. For ease of illustration, the X-loops 150a-150c are shown as staggered laterally such that each of the X-loops 150a-150c is aligned parallel to the major X axis, but offset laterally relative to a neighboring X-loop 150a-150c. In a similar manner, the Y-loops 160 are formed of electrical wires or printed circuitry such that the Y-loops 160 overlap. The Y-loops 160a-160c are aligned parallel to the major Y axis, and staggered such that each Y-loop 160a-160c is vertically offset (relative to the orientation of FIG. 5) relative to a neighboring Y-loop 160a-160c. In this regard, each Y-loop 160 is aligned parallel to the major Y axis and staggered relative to the central Y-loop 160a.

Figure 6:
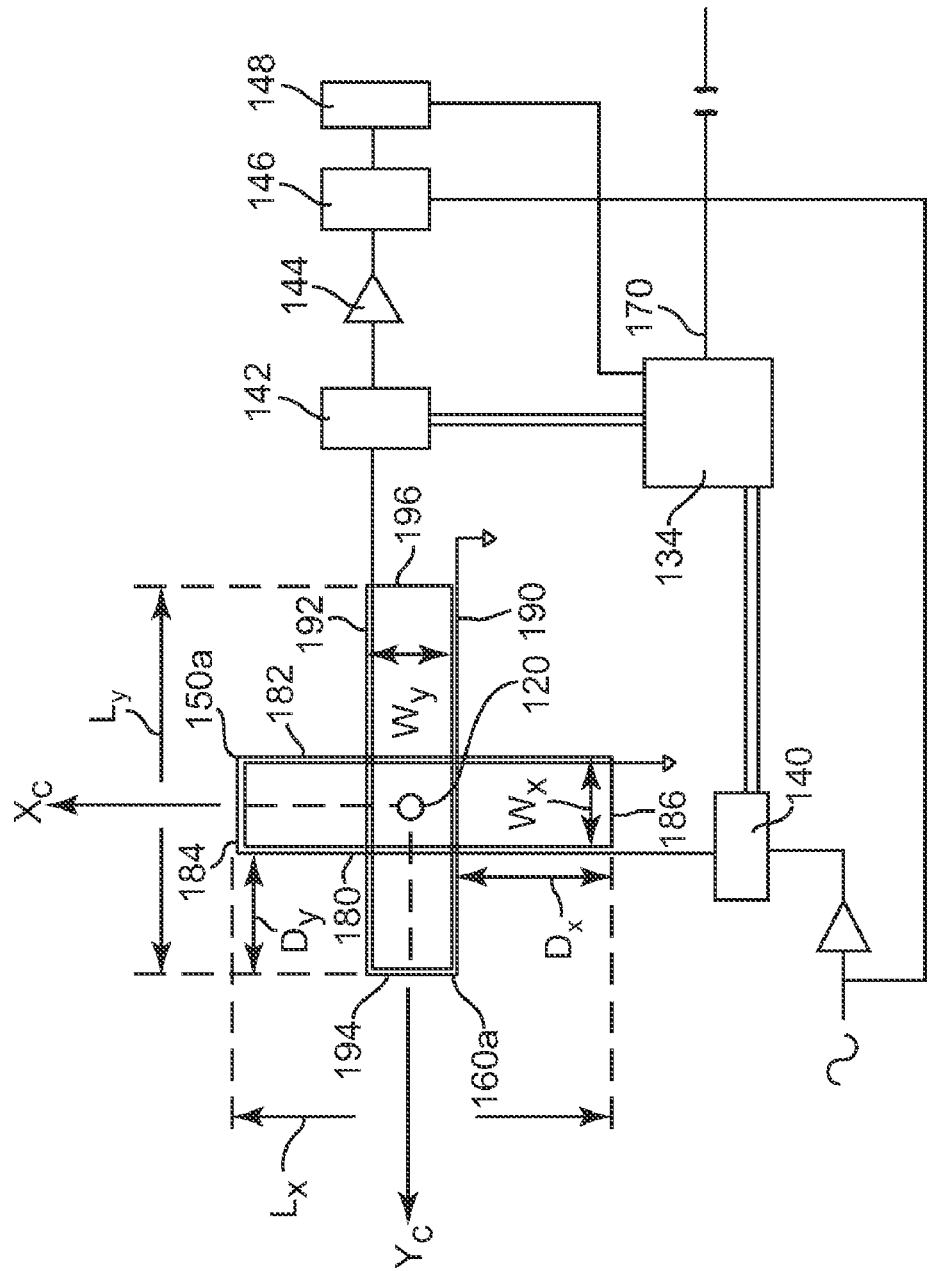
FIG. 6 is a simplified schematic illustration of one X-loop and one Y-loop of the circuitry illustrated in FIG. 5.

FIG. 6 illustrates a simplified schematic view of the central X-loop 150a and the central Y-loop 160a. In general terms, each of the X-loops 150 are highly similar, and in this regard, will be described with reference to the central X-loop 150a. The central X-loop 150a is generally a rectangular loop that defines a first side 180 opposite a second side 182, and opposing ends 184, 186. The opposing sides 180, 182 are generally parallel to the major X axis (FIG. 5), and thus parallel and oriented relative to the central axis $X_C$, and have a length of $L_X$. The opposing ends 184, 186 are generally orthogonal to the opposing sides 180, 182, and orthogonal to the central axis $X_C$, and define a width of $W_X$. In this manner, the opposing ends 184, 186 are parallel to a minor axis of the rectangular central X-loop 150a.

In one embodiment, the length $L_X$ of the central X-loop 150a can be about a factor of two longer than a width $W_X$ of the loop 150a. Current flowing through the central X-loop 150a creates an electromagnetic field that can potentially interfere with the current flowing in the Y-loops 160 (such as the central Y-loop 160a). For this reason, the opposing ends 184, 186 are printed or otherwise wired/disposed to be offset from the central Y-loop 160a by a distance $D_X$. In one embodiment, the distance $D_X$ is greater than about 0.5 inches, and preferably greater than about 1.0 inches to minimize the effect that current flowing in the ends 184, 186 might potentially have on the central Y-loop 160a.

Each of the Y-loops 160 are in general highly similar, and in this regard will be described with reference to the central Y-loop 160a. The central Y-loop 160a is generally a rectangular loop that defines a first side 190 opposite a second side 192, and opposing ends 194, 196. The opposing sides 190, 192 are generally parallel to the major Y axis (FIG. 5), and thus parallel relative to the central axis $Y_C$, and have a length of $L_y$. The opposing ends 194, 196 are generally orthogonal to the opposing sides 190, 192, orthogonal to the central axis $Y_C$, and define a width of $W_y$. In this manner, the opposing ends 194, 196 are parallel to a minor axis of the rectangular central Y-loop 160a.

In one embodiment, the length $L_y$ of the central Y-loop 160a can be about a factor of two longer than a width $W_y$ of the loop 160a. Current flowing through the central Y-loop 160a creates an electromagnetic field that can potentially interfere with the current flowing in the X-loops 150. For this reason, the opposing ends 194, 196 are printed or otherwise wired/disposed to be offset from the central X-loop 150a by a distance $D_y$. In one embodiment, the distance $D_y$ is greater than about 0.5 inches, and preferably greater than about 1.0 inches to minimize the effect that current flowing in the ends 194, 196 might potentially have on the central X-loop 150a.

With additional reference to FIG. 5, the locator grid 136 optionally includes a plurality of interleaved X-loops 150 and a plurality of interleaved Y-loops 160. In this specification, the term "interleaved" refers to a loop that overlaps but is offset from a neighboring loop. For example, the central X-loop 150a is aligned along the central axis $X_C$, and the second X-loop 150b is interleaved with the central X-loop 150a in that the second X-loop 150b overlaps but is offset to the left (with reference to the orientation of FIG. 5) to the central X-loop 150a. In a like manner, the third X-loop 150c is interleaved relative to the central X-loop 150a. Consistent with this definition of interleaved, it is noted that the central X-loop 150a is looped around a region, or a boundary, that coincides with a portion of the second X-loop 150b and a portion of the third X-loop 150c. To this end, the needle opening 120, which is disposed centrally relative to the central X-loop 150a, is also within the boundaries of the second X-loop 150b and the third X-loop 150c. A similar interleaved relationship is established for the Y-loops 160. By virtue of the interleaved nature of the plurality of X-loops 150 and the plurality of Y-loops 160, a current sequentially supplied to the X-loops 150, for example, will enable each of the X-loops 150 to individually energize a coil, such as the coil(s) 32 (FIG. 1), to varying degrees (where a position of the coil 32 is otherwise relatively stationary relative to the X-loops 150 during sequential powering). Further, the interleaved nature promotes iterative sampling of voltage signals sensed by the receive loops (i.e., the Y-loops 160, as well as the X-loops 150 with active constructions).

Figure 7:
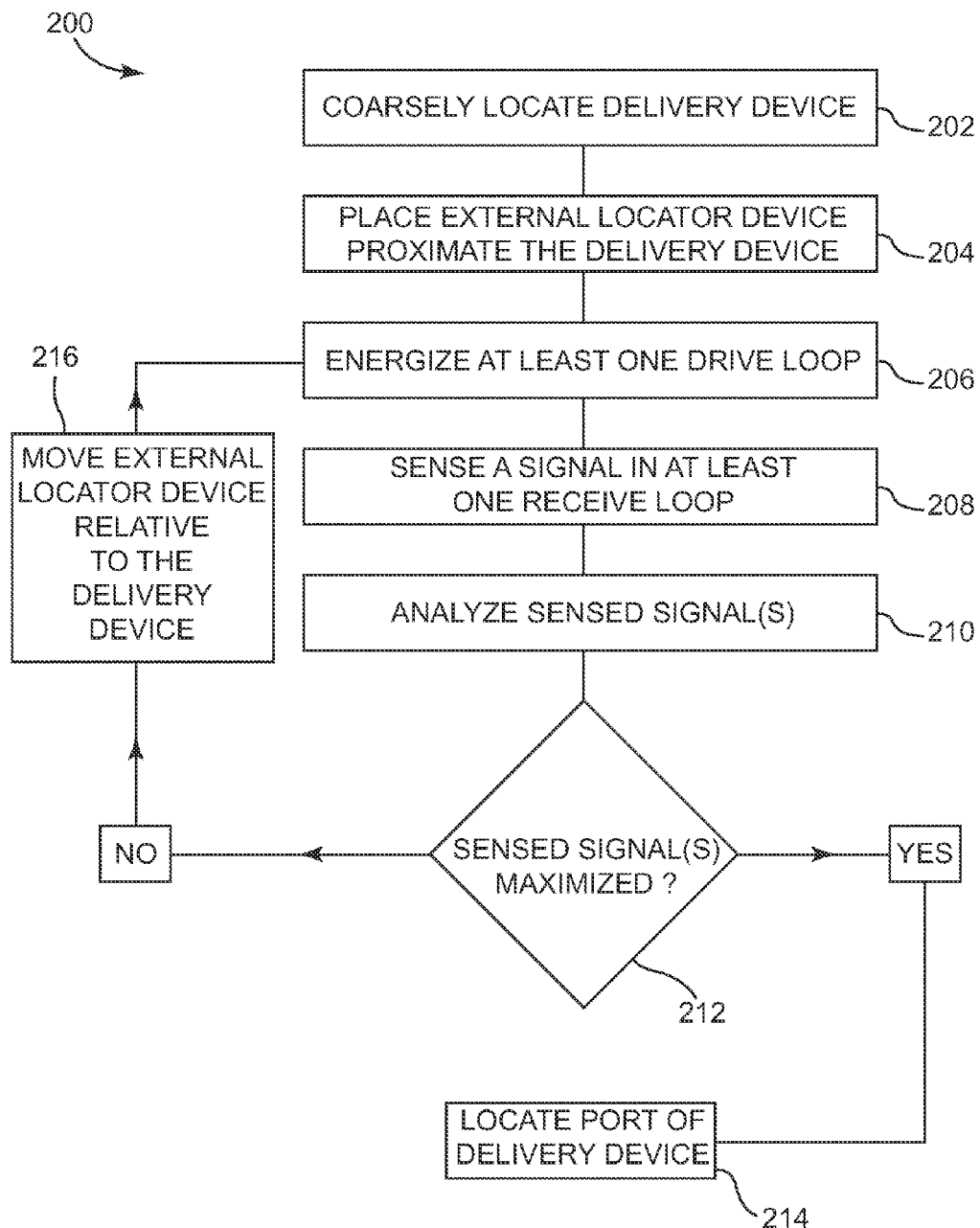
FIG. 7 is a flow diagram of a method of percutaneously locating a port opening of an implantable medical device in accordance with principles of the present disclosure.

During use, and returning to FIG. 1, the implantable substance delivery device 24 is implanted to the patient 22 in accordance with acceptable techniques. Subsequently, it may be necessary to percutaneously interact with the fill port assembly 28 (e.g., a reservoir refill procedure) or the catheter access port assembly 30 (e.g., for direct delivery of liquid to the patient 22). Under these and other circumstances, the clinician may desire to accurately determine, percutaneously, a location of the desired port opening 84 or 94. FIG. 7 illustrates a flow diagram for a method 200 of locating a port opening of the implantable delivery device 24 in accordance with principles of the present disclosure. As a point of reference, and with combined reference to FIG. 1, the methodology described below relates to a passive configuration of the system 20 (i.e., where the coil(s) 32 carried by the implantable delivery device 24 are not directly powered by the device's 24 power supply). An explanation of operation using an active configuration is separately provided. In general terms, the method 200 is premised upon locating a center of one or more of the coil(s) 32 provided with the delivery device 24. Thus, the methodology can vary depending upon whether the port opening 84 or 94 to be located has a coil 32' co-axially disposed thereabout (e.g., FIG. 3A), or if the coil(s) 32 are off-set from the port opening 84 or 94 at a known location (e.g., FIG. 1).

At step 202, the delivery device 24 is coarsely located, for example by a clinician palpating the implant site to identify the general location of the device 24. Thereafter, the external locator device 26 is, then, at step 204, placed proximate the delivery device 24 based upon the identification of the general location of the device 24 derived at step 202.

The drive loop(s) 150 of the external locator device 26 are then selectively energized at a desired frequency at step 206. At step 208, the receive loops 160 are polled and any signal (resulting from the induced energization of a coil 32 proximate the energized drive loop 150) is noted. The sensed are analyzed at step 210. In this regard, and as detailed above, the sensed signal in the receive loops 160 is maximized when the coil 32 being located is aligned with the central X-loop 150a and the central Y-loop 160a, which therefore aligns the needle opening 120 (disposed at the intersection of the central X-loop 150a and the central Y-loop 160a) with the coil 32 being located.

If it is determined at step 212 that the signal(s) in the receive loop(s) 160 are in-phase and at a relative (local) maximum, the center of the coil 32 being located has been "located" and is used to dictate locating of the needle opening 120 over the port opening 84 or 94 desired. Conversely, if a maximum receive signal is not found, step 216 provides for iteratively energizing 206, sensing 208, and analyzing 210 output signals for a different location of the external locator 26 relative to the delivery device 24 (and in particular the coil 32 being located) until step 212 is satisfied. As described above, the visual indicator 122 (FIG. 4) provides output relative to the sensed signals that is useful in guiding the clinician in determining in which direction the external locator device 26 is to be moved.

Figure 8A:
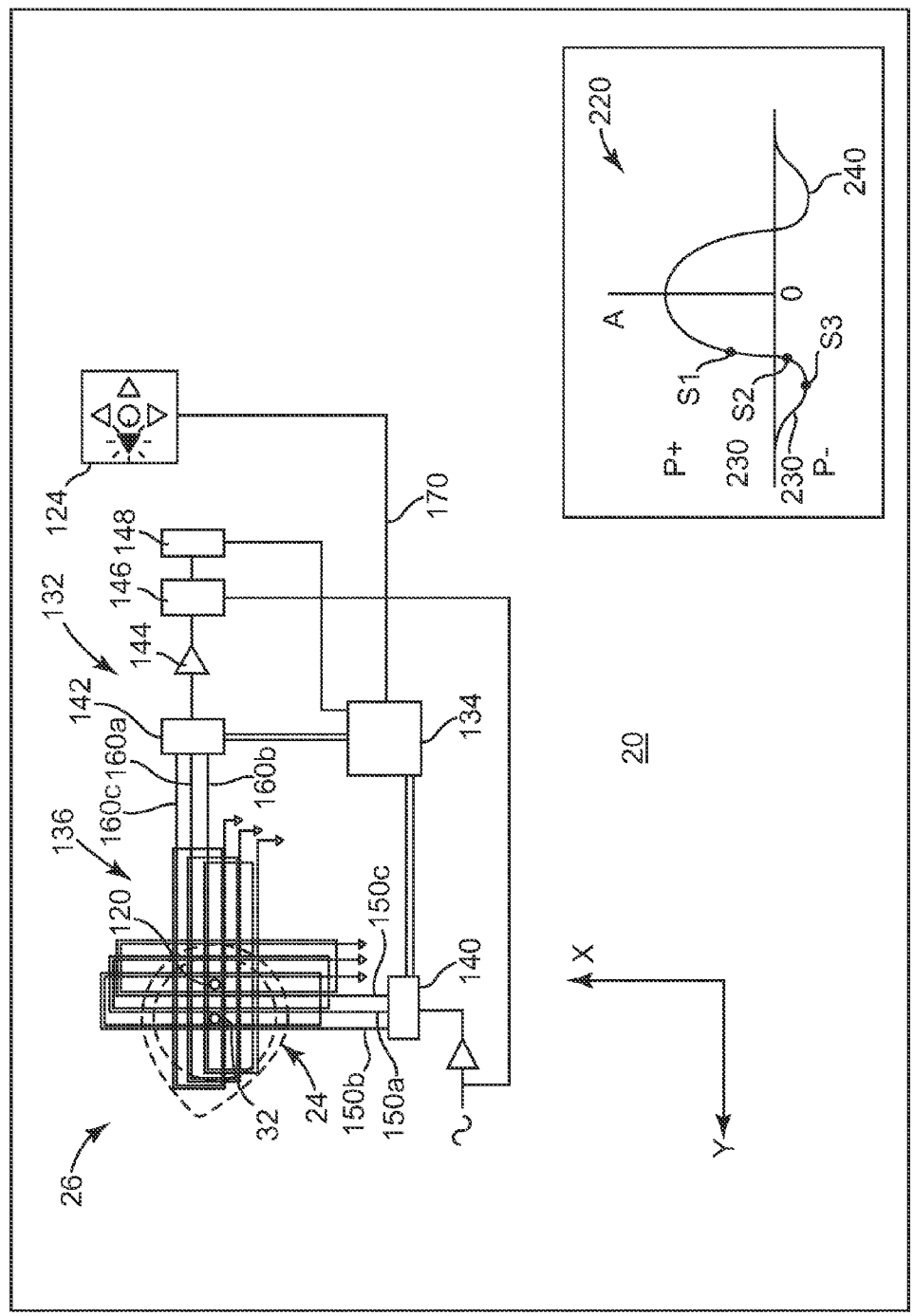
FIG. 8A is a simplified schematic view of a system for locating a port opening of an implantable medical device with a locator device in accordance with the method of FIG. 7.

The iterative process of repeatedly energizing selected ones of the drive or X-loops 150 (at the frequency "tuned" to the particular coil 32 being located), with each of the receive or Y-loops 160 then being sampled at each X-loop 150 energization in "locating" a center of the coil 32 of interest can be explained by the relatively simplistic example of FIG. 8A. As a point of reference, the implantable delivery device 24 is illustrated in broken lines in FIG. 8A to reflect an implanted position. In this regard, the delivery device 24 is spaced apart from the external locator device 26 such that a relative size of the coil 32 is not necessarily to scale with a size of the needle opening 120. Further, with the one example of FIG. 8A, the coil 32 being located is co-axially disposed about the fill port opening 84 (such that locating a center of the coil 32 directly locates the fill port opening 84 and proper positioning of the needle opening 120), it being understood that in other embodiments, the coil(s) 32 need not be co-axially positioned about the desired port opening 84 or 94 (FIG. 1). With these other embodiments, however, the center of the coil(s) 32 will still be located or "found" in a similar manner to that described below. The external locator 26 has been simplified in the view of FIG. 8A for ease of illustration to generally illustrate a portion of the circuitry 132 and the locator grid 136, although it is to be understood that the case 130 (FIG. 4) would ordinarily contain and obstruct these components from view.

An arbitrary X-Y axis is provided in FIG. 8A for illustrative purposes. The orientation of the X-Y axes has been chosen such that the X-axis is parallel with the X-loops 150a-150c and the Y-axis is parallel to the Y-loops 160a-160b, although with other orientations are also acceptable. With the above conventions in mind, the external locator device 26 is moved over the delivery device 24 to generate sensed output signals and identify a position of the needle opening 120 relative to the coil 32 (and thus relative to the fill port opening 84).

In some embodiments, the remote visual indicator 124 graphs/plots a profile 220 that represents a composite accumulation of possible output signals sensed in the receive loops 160 (for example, the Y-loops 150a-150c). Profile 220 provides an amplitude A and phase P profile, where positive amplitudes A are represented on the vertical axis, in-phase (P+) signals are plotted above the horizontal axis, and out-of-phase (P−) signals are plotted below the horizontal axis. One useful interpretation of the profile 220 is understood by viewing the profile 220 to be imposed over the locator grid 136 when the locator grid 136 is viewed on-end. For example, imposing the profile 220 onto the locator grid 136 such that the amplitude A projects out of the paper (relative to the X-Y axis shown in FIG. 8A), and such that the amplitude A vertical axis is aligned relative to the central X-loop 150a, will result in the composite signal having a maximum amplitude A aligned centrally on the central X-loop 150a and with the needle opening 120. Imaginary vertical slices taken parallel to the amplitude A axis will intersect the profile 220, and each intersection represents a signal strength (as received by the Y-loops 160) of an X-loop that is displaced away from the central X-loop 150a. As the X-loops 150 are selected and energized (and corresponding Y-loop 160 receive signals are sensed) that are away from the central X-loop 150a, the received amplitude A decreases, eventually passing through zero, to define lobes 230, 240. The lobes 230, 240 represent out-of-phase (P−) signals.

In the simplified example of FIG. 8A, the coil 32 is located centrally within the central Y-loop 160b, such that the following description relates to locating of the coil 32 (and moving of the locator device 26) in the Y-axis. It is to be understood that the locator grid 136 includes many multiple X-loops 150 and multiple Y-loops 160, only a select few of which are shown for ease of illustration. Further, the following description applies equally to the case when the coil 32 is located elsewhere. That is to say, the coil 32 being located can instead be centrally positioned to another one of the many Y-loops 160 at the start of the location procedure, and the controller 134 is adapted to select the appropriate, or preferred, Y-loop 160 that is to be selected as the receive loop signal being analyzed for purposes of Y-axis positioning.

Having thus coarsely identified a spatial placement of the coil 32 as central to one Y-loop (e.g., the central Y-loop 150a), the controller 134 iteratively and selectively determines in which X-loop 150 the coil 32 is located. As a point of reference, in the view of FIG. 8A, the coil 32 is within the second X-loop 150b, just outside of the central X-loop 150a, and relatively substantially outside of the third X-loop 150c, the exact location of which is determined in the following manner.

One exemplary iterative process includes sequentially energizing each of the X-loops 150 to energize the coil 32 and induce a voltage in the selected Y-loop 160 (e.g., the central Y-loop 160a in FIG. 8A). Each resulting output signal, or receive signal in the central Y-loop 160a, is ratio metrically analyzed to determine which of the X-loops 150 is associated with the output signal having the largest amplitude. In this manner, the coil 32 can be "located" within one of the X-loops 150a-150c based upon a comparison of the resulting sequential signals sensed in the selected receive loop (the central Y-loop 160a in this example).

Specifically, a distribution of the X-loops 150a-150c is selected and sequentially driven (or energized) by operation of the controller 134, the distribution being preferably around or distributed about the coil 32. Since the locator grid 136 includes many X-loops, such a distribution about the coil 32 is easily identified by the controller 134. One example of such a distribution can include sequential driving or energization of the second X-loop 150b, then the central X-loop 150a, followed by the third X-loop 150c. To this end, each of the X-loops 150 is energized/driven with a current (at the predetermined frequency associated with the trunk circuit of the coil 32). Since the X-loops 150 are oriented orthogonally to the Y-loops 160, the X-loops 150, and the Y-loops 160 are electrically decoupled. Relative to the coil 32/locator grid 136 relationship of FIG. 8A, the field created by the energized second X-loop 150b energizes the coil 32, which in turn induces a voltage in the selected receive loop (the central Y-loop 160a) that is read as signal 51 by controller 134. Because the coil 32 is within the second X-loop 150b and within the central Y-loop 160a, the resulting signal 51 has a positive amplitude that is in-phase, and shifted off of the central axis of profile 220.

Next, the central X-loop 150a is driven with a current (at the selected frequency), thus energizing the coil 32 and inducing a voltage in the central Y-loop 160a that is read by the controller 134 as signal S2. Since the coil 32 is "outside" of the central X-loop 150a, the signal S2 is out-of-phase and has a negative amplitude A.

Next, the third X-loop 150c is sequentially driven with a current (at the selected frequency) to energize the coil 32 and induce a voltage in the central Y-loop 160a that is read by the controller 134 as signal S3. Since the coil 32 is relatively substantially outside of the third X-loop 150c, the signal S3 has a more pronounced negative amplitude and is further out-of-phase.

With the above data in hand, a fine position of the location of the coil 32 is determined by a ratio metric algorithm that weighs or analyzes the relative magnitudes of the received signals S1-S3 in determining a relative location of the coil 32 relative to the driven X-loops 150a-150c and thus relative to the needle opening 120. Those with skill in the art of signal analysis will readily recognize that any number of suitable mathematical functions are available that will analyze the received signals S1-S3 to determine a relative location of the coil 32 relative to the locator grid 136. Ultimately, the controller 134 communicates with the visual indicator 122 through the output line 170 to provide information to the clinician, such as which direction the external locator 26 should be moved to align the needle opening 120 with the coil 32 (with embodiments in which the coil 32 is co-axially disposed about the desired port opening). In this example, signals S1-S3 combine to indicate that the coil 32 is to the left (i.e., along the Y axis) relative to the central X-loop 150a (and thus relative to the needle opening 120), such that the external locator 26 should be moved left, or in the direction of the positive Y axis direction. In other words, the controller 134 determines that the needle opening 120 should be moved in a direction that aligns the central X-loop 150a relative to where the largest signed amplitude S1 was sensed (i.e., needle opening 120 should be moved left). As a point of reference, for embodiments in which the coil(s) 32 being located are off-set from the port opening 84 or 94 (FIG. 1) of interest at a known location, the coil 32 is located as described above, and then an algorithm is employed to mathematically determine a location of the desired port opening 84 or 94 based upon the now "known" location of the coil(s) 32.

One embodiment of locating the coil 32 relative to the driven X-loops 150 (i.e., locating the coil 32 in the X axis) has been described above in which multiple X-loops 150 are sequentially driven to induce a voltage in one receive loop (e.g., the central Y-loop 160a). A position of the coil 32 relative to the receive Y-loops 160 (i.e., locating the coil 32 in the Y axis) is derived by driving one of the X-loops 150, and sensing and comparing the resultant, induced voltage signals in multiple receive loops 160. Appropriate analysis of the signals induced in the multiple receive loops 160 enables the controller 134 to determine a relative position of the coil 32 with respect to the Y-loops 160. A composite profile based on the output of the multiple receive loops 160 will produce the same relative representation of the phase and amplitude profile 220. That is to say, sequentially driving multiple X-loops 150 and sensing a signal in one selected receive loop 160 (to fix a location of the coil 32 relative to the X-loops 150) provides a symmetrically equivalent amplitude and phase profile 220 as is derived by driving a single drive loop 150 and sequentially sensing signals in multiple receive loops 160 (to determine a location of the coil 32 relative to the Y-loops 160). Thus, for example, where the coil 32 is located within the central X-loop 150 and centrally within the second Y-loop 160b, within but off-center from the central Y-loop 160a, and outside of the third Y-loop 160a, the output induced signals/voltages from the Y-loops 160a-160c in response to energization of the central X-loop 150a will reflect this positional relationship (i.e., the signal analysis of the Y-loops 160a-160c responsive to energization of only the central X-loop 150a will reflect in-phase signals for the central and second Y-loops 160a, 160b, with the second Y-loop 160b signal having a greater amplitude, and the third Y-loop 160c will have an out-of-phase signal).

Figure 8B:
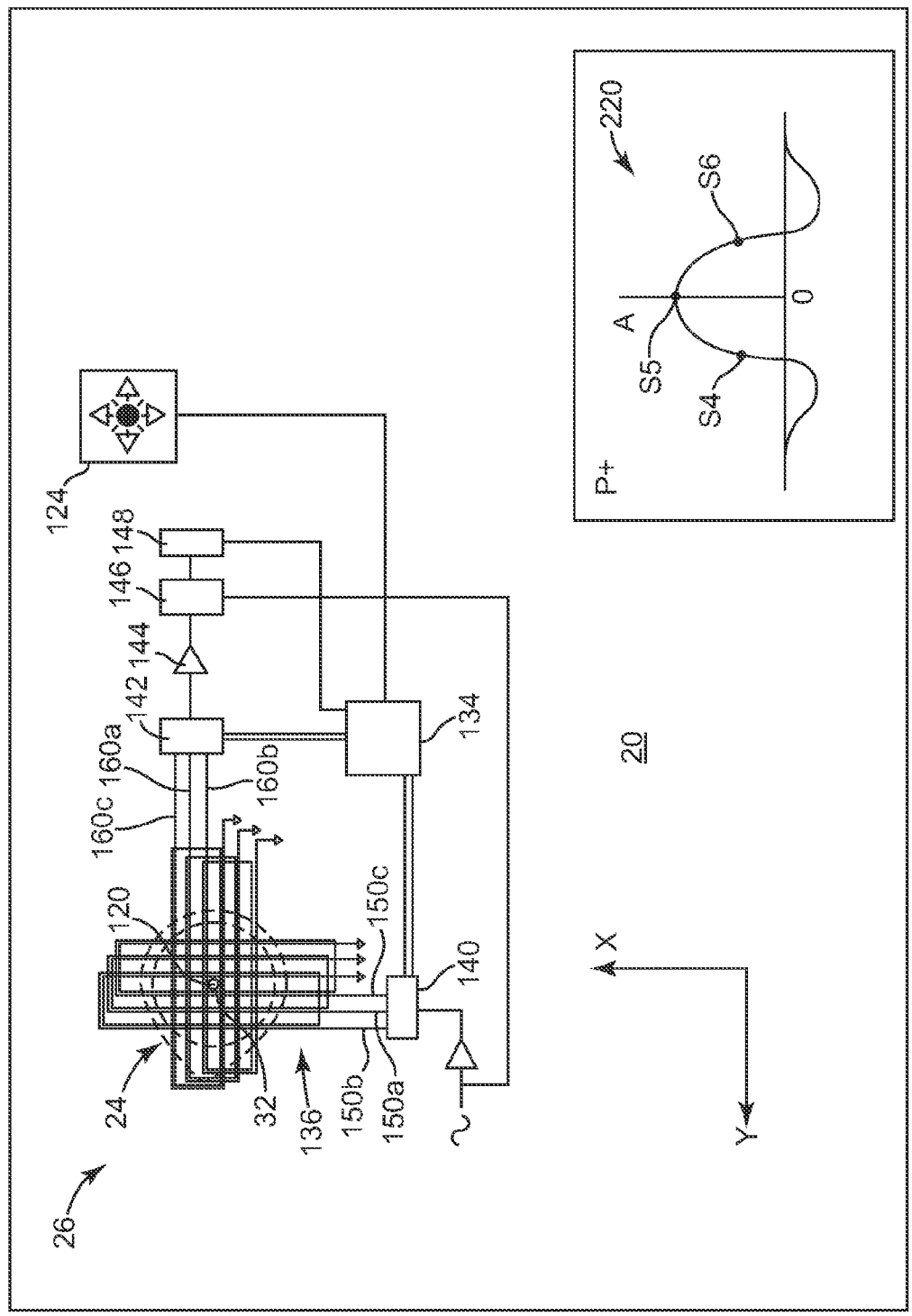
FIG. 8B illustrates the system of FIG. 8A following completion of the method of FIG. 7.

As a point of reference, FIG. 8B illustrates the system 20 with the locator grid 136 now aligned over the coil 32 being located (and, with the one embodiment, the fill port opening 84 of interest). The needle opening 120, which is centered in the central X-loop 150a and the central Y-loop 160a, is aligned above the coil 32. Confirmation of this one desired location can be achieved as follows. The second X-loop 150b is energized/driven with a current that energizes the coil 32, which in turn induces a voltage in the central receive loop 160a that is read as signal S4 by the controller 134. Because the coil 32 is within the second X-loop 150b and within the central Y-loop 160a, the resulting signal S4 has a positive amplitude that is in-phase, and shifted off of the central axis of profile 220. Next, the central X-loop 150b is energized with a current that energizes the coil 32 and induces a voltage in the central Y-loop 160a that is read by the controller 134 as signal S5. Since the coil 32 is centrally located within both the central X-loop 150a and the central Y-loop 160a, the signal S5 is sensed as an in-phase signal having a maximum amplitude A. Next, the third X-loop 150c is driven with a current to energize the coil 32 that induces a voltage in the central Y-loop 160a that is read by the controller 134 as signal S6. Since the coil 32 is within, but off center, relative to the third X-loop 150c, the signal S6 is similar to the signal S4 and has a positive amplitude of similar magnitude that is in-phase, but shifted off of the central axis to an opposing side of profile 220. Since the coil 32 is within each of the X-loops 150a-150c the resulting signals S4, S5, S6 are all in-phase and have a positive amplitude.

In a similar manner, a position of the coil 32 is determined relative to the receive loops (Y-loops 160a-160c) by driving one selected drive loop 150 (for example, the controller 134 could determine that driving the central X-loop 150a is optimal as the central X-loop 150a is centrally aligned over the coil 32) to induce voltages in the multiple receive loops 160a-160c. Following a similar manner of signal interpretation, the controller 134 will determine the coil 32 to be centrally located relative to the central Y-loop 160a. In particular, the controller 134 reads and analyzes each of the resulting multiple receive signals to determine that the coil 32 is centrally located underneath the needle opening 120 (or otherwise identified relative to the locator grid 136). In some embodiments, this confirmation can be provided by the visual indicator 122 that otherwise indicates the locator device 26 is centered over the coil 32, thus indicating that the needle opening 120 is aligned over the desired port opening (e.g., the fill port opening 84). Once again, with embodiments in which the coil(s) 32 being located are off-set from the desired port opening 84 or 94 (FIG. 1), the locator device 26 operates to guide the needle opening 120 over the port opening 84 or 94 once all of the coils 32 have been located.

As indicated by the above, phase information is employed, in some embodiments, as a reference point to determine whether the coil 32 being located is within or outside of an X-loop 150/Y-loop 160 signal pair being analyzed. To this end, continuous phase information is not of primary importance; rather, a determination is made as to whether the received signal is in-phase (zero) or 180 degrees out-of-phase. For example, in instances where the coil 32 being located is within both the driven X-loop 150 and the analyzed receive Y-loop 160 being analyzed, the resultant signal will be in-phase; conversely, where the coil 32 is inside only one of the driven X-loop 150 or the analyzed receive Y-loop 160, the resultant signal will be 180 degrees out-of-phase. It is recognized that where the coil 32 being located is outside both of the driven X-loop 150 and the analyzed receive Y-loop 160, two negatives would result in a positive phase. To address the potentially misleading phase information, the system and methods of the present disclosure can include repeatedly scanning through all drive and receive information generated by the multiple X-loop 150/Y-loop 160 combinations. Once a receive loop 160 signal is first received (i.e., as the locator device 26 is initially moved in close enough proximity to the coil 32 being located that energization of any of the X-loops 150 results in some induced voltage or signal at one of the Y-loops 160), the drive loop 150/receive loop 160 combinations adjacent the drive loop 150/receive loop 160 combination generating the initial signal are scanned. At some point, other in-phase combinations will be located. The coil 32 can positively be determined as being within the in-phase combination having the highest amplitude. Subsequent "narrowing" of an exact location of the coil 32 can then occur as described above.

Figure 8C:
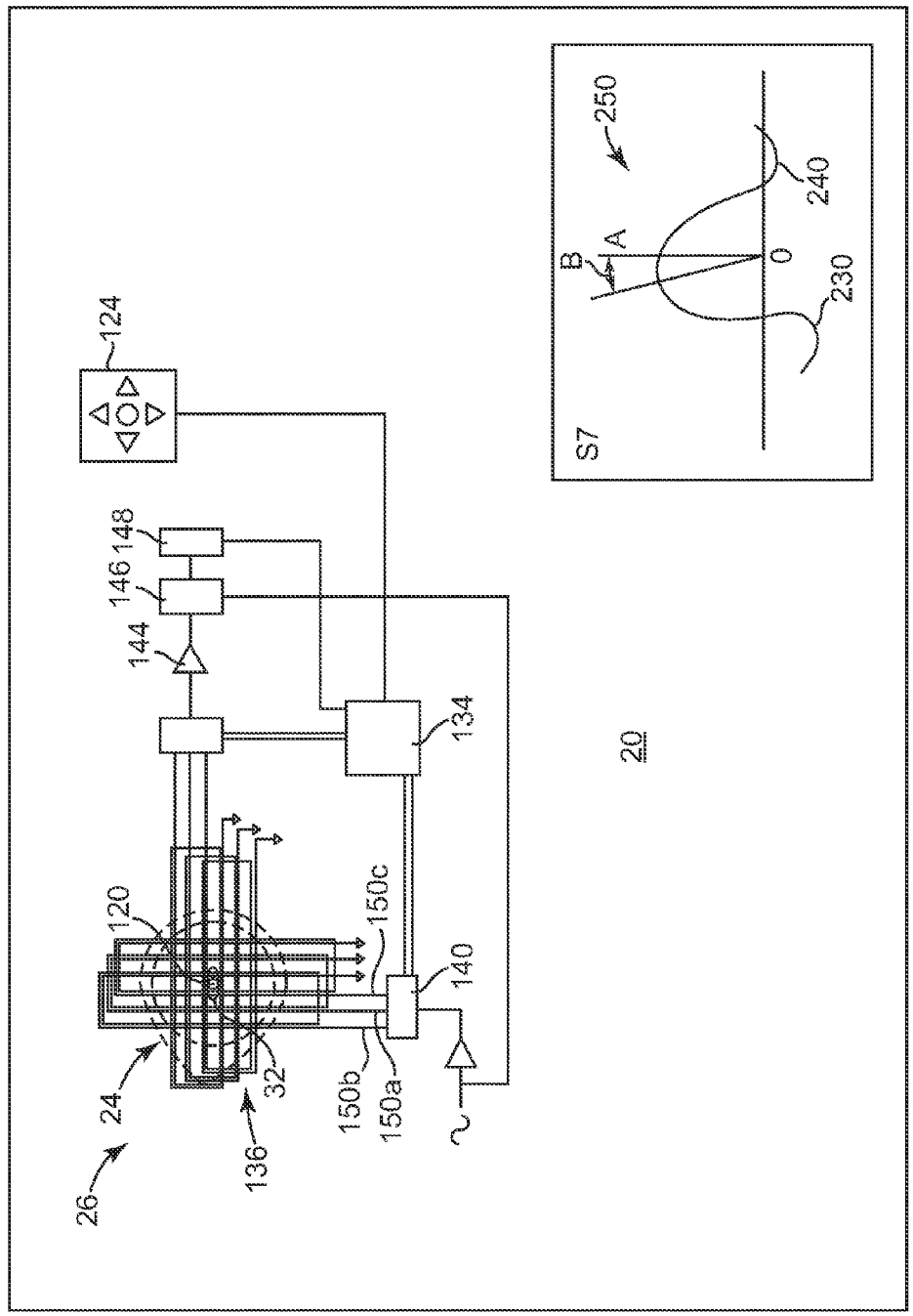
FIG. 8C illustrates the system of FIG. 8A in detecting a tilt in the port opening.

Phase information can further assist in accounting for circumstances in which the delivery device 24 is tilted, or becomes tilted, relative to the patient 22 site (FIG. 1) as represented by the simplified example of FIG. 8C. Consequently, the coil 32 is also tilted. The relative tilt in the coil 32 induces a voltage in a selected receive loop 160 that results in a phase profile 250 that is tilted relative to the received amplitude A axis. In this regard, the coil 32 is illustrated as oval-shaped in FIG. 8C to indicate that that a central axis of the coil 32 "leans" toward the second X-loop 150b.

The phase profile 250 is tilted by an angle B relative to the received amplitude A axis, which indicates that a central axis the coil 32 being located, is also tilted by the angle B relative to the external locator device 26 (FIG. 1). The asymmetry of the phase profile 250 is detectable by the controller 134 and useful in calculating the amount of tilt in the coil 32. The combined sensed signals S7 generated by driving the second X-loop 150b has a large out-of-phase portion (lobe 230) in the direction toward the loop 150 or 160 to which the coil 32 is tilted. For example, when the coil 32 is tilted by the angle B to the left toward a peripheral loop, such as the second X-loop 150b, the left edge of the coil 32 becomes closer to the outside edge of the second X-loop 150b and outputs (at the Y-loops 160) a relatively larger amplitude that is 180 degrees out-of-phase to the left (i.e., lobe 230) of the phase profile 250. In some embodiments, this phase profile (or other representation thereof) can be conveyed by the visual indicator 124. Seeing this output on the remote visual indicator 44, the clinician is prompted to alter the orientation of the external locator 26 relative to the patient 22 site (FIG. 1) until the out-of-phase portions of lobes 230, 240 are balanced.

Other construction can also be employed to facilitate the optional device 20 tilt evaluation or determination. For example, the locator grid 136 can include one or more Z-axis loops (i.e., relative to the X, Y coordinates of FIG. 5, the additional Z-axis loop(s) would be oriented perpendicular to the plane of the drawing, and thus perpendicular to the X-loops 150 and the Y-loops 160). During use, the Z-axis loop(s) would effectively be perpendicular to a face of the external locator 26, and thus a voltage induced therein (if any) by the coil 32 (FIG. 1) being located would provide information indicative of an angular orientation of the coil 32 relative to the Z-axis loop (and thus of the port opening 84, 94 being located relative to the locator device 26). Iterative determination or alignment of the Z-axis loop(s) relative to the coil(s) 32, and thus relative to the port opening 84, 94 in question, could be performed akin to the techniques described above. This tilt information, in turn, can be conveyed to the user, for example via a visual indication that the locator device 26 should be tilted relative to the patient 22 (FIG. 1) to better ensure an aligned relationship between the needle opening 120 (FIG. 1) and the port opening 84, 94 in question.

Regardless of whether tilt determination is an included feature, the above methods of operating the system 20 in locating a desired port opening relate to passive constructions (i.e., where the coil(s) 32 being located are not powered by the implantable medical device 24, but instead induced voltages are generated upon energization of the drive or X-loops 150). Active constructions operate in a relatively similar manner. More particularly, the coil(s) 32 being located is/are energized by a power source/internal circuitry provided by or with the implantable medical device 24. As such, the X-loops 150 need not be "driven," but instead operate as receive loops, as do the Y-loops 160. The signals received at the X-loops 50 are analyzed, as are the signals at the Y-loops 160. In this regard, phase reference information is not available. However, by scanning through all of the X-loops 150, a collective signal profile or signature is generated, characterized by a peak and opposing decays. The coil 32 being located can then be designated as being most closely centered relative to the X-loop 150 generating the peak value. A more precise position can be determined by employing a ratio metric algorithm utilizing the amplitude of the peak loop and the two adjacent loops on either side of the peak loop. A similar scanned signal signature analysis is performed relative to the signals generated at the Y-loops 160.

The system and method of the present disclosure provides a marked improvement over previous designs. Aspects of the present disclosure provide a convenient and accurate method by which a clinician is able to identify a location of either a fill port assembly or a catheter port assembly within an implanted medical device. In particular, aspects of the present disclosure provide an external locator device usable by the clinician that is adapted to accurately identify a location of a coil that is positioned at a known location relative to a port opening of the medical device, and by accurately identifying the location of the coil, the clinician is able to locate the port opening (and thus the septum disposed within the corresponding port). Other aspects of the present disclosure provide visual indicators to the clinician that guide the movement of the external locator device relative to the implanted medical device to assist the clinician in quickly identifying and verifying a location of the desired port/port openings.

Although the present disclosure has been described with reference to preferred embodiments, workers skilled in the art will recognize that changes can be made in form and detail without departing from the spirit and scope of the present disclosure.

What is claimed is:

1. A locator device for externally detecting a coil carried by a substance delivery device implanted within a patient, the locator device comprising:
   a controller; and
   a locator grid including:
      a plurality of interleaved X-loops electrically coupled to the controller, each of the X-loops defining a major axis that is oriented parallel to a first major axis,
      at least one Y-loop electrically coupled to the controller and oriented along a second major axis differing from the first major axis;
   wherein the locator device is configured such that when the locator device is spatially proximate the coil, energization of the coil induces a voltage in the at least one Y-loop that is read by the controller, and further wherein the controller is adapted to determine a location of the coil relative to the locator grid based upon the read voltage.

2. The locator device of claim 1, wherein the plurality of X-loops includes a central X-loop oriented along a first central axis and the at least one Y-loop comprises a central Y-loop oriented along a second central axis, and further wherein the locator device defines a needle opening extending through a housing of the locator device at a location where the first central axis intersects the second central axis.

3. The locator device of claim 1, wherein the second central axis is orthogonal to the first central axis.

4. The locator device claim 1, wherein each of the X-loop is staggered relative to, and overlaps, a neighboring X-loop.

5. The locator device of claim 1, wherein the locator grid includes a plurality of Y-loops, each Y-loop including a major axis that is parallel to the second major axis such that each Y-loop is staggered relative to a neighboring Y-loop.

6. The locator device of claim 5, wherein the plurality of Y-loops are interleaved.

7. The locator device of claim 6, wherein the plurality of X-loops are electrically decoupled from the plurality of Y-loops.

8. The locator device of claim 1, wherein at least one of the plurality of X-loops comprises a rectangular loop defining a first side opposite a second side and opposing ends, the first and second sides being parallel to the first major axis and the opposing ends being parallel to a minor axis of the at least X-loop, the minor axis being orthogonal to the first major axis.

9. The locator device of claim 1, wherein the locator device further includes a power source.

10. The locator device of claim 9, wherein the locator device is adapted such that when the locator grid is positioned proximate the coil and a current is applied to one of the plurality of X-loops, the coil is energized and a voltage is induced in the at least one Y-loop.

11. The locator device of claim 10, wherein at least one Y-loop includes a plurality of Y-loops, and further wherein the controller is adapted to iteratively sample and compare signals generated at each of the Y-loops in at least partially determining a location of the coil relative to the locator grid.

12. The locator device of claim 11, wherein the coil is passively energized by the X-loop, and further wherein the controller is adapted to sequentially power respective ones of the plurality of X-loops and iteratively compare signals generated at a selected one of the Y-loops in at least partially determining a location of the coil relative to the locator grid.

13. The locator device of claim 11, wherein the controller is adapted to output amplitude and phase information of signals that are induced in at least one of the plurality of Y-loops.

14. The locator device of claim 1, wherein the plurality of X-loops includes a central loop and adjacent loops positioned at opposite sides, respectively, of the central loop, and further wherein the controller is adapted to estimate a tilt of an implantable substance delivery device relative to the locator grid based upon evaluation of symmetry of induced voltages at the central loop and the adjacent loops.

* * * * *